United States Patent
Sommer et al.

(10) Patent No.: US 11,226,389 B2
(45) Date of Patent: Jan. 18, 2022

(54) COMBINED ARTERIAL SPIN LABELING AND MAGNETIC RESONANCE FINGERPRINTING

(71) Applicant: KONINKLIJKE PHILIPS N.V., Eindhoven (NL)

(72) Inventors: Karsten Sommer, Hamburg (DE); Michael Gunter Helle, Schleswig-Holstein (DE); Thomas Erik Amthor, Hamburg (DE); Peter Boernert, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 466 days.

(21) Appl. No.: 16/339,858

(22) PCT Filed: Oct. 9, 2017

(86) PCT No.: PCT/EP2017/075614
§ 371 (c)(1),
(2) Date: Apr. 5, 2019

(87) PCT Pub. No.: WO2018/065618
PCT Pub. Date: Apr. 12, 2018

(65) Prior Publication Data
US 2020/0050819 A1   Feb. 13, 2020

(30) Foreign Application Priority Data
Oct. 7, 2016   (EP) ...................................... 16192733

(51) Int. Cl.
*G01R 33/563* (2006.01)
*A61B 5/00* (2006.01)
(Continued)

(52) U.S. Cl.
CPC ........ *G01R 33/5635* (2013.01); *A61B 5/0042* (2013.01); *A61B 5/0263* (2013.01);
(Continued)

(58) Field of Classification Search
CPC ..... A61B 5/0263; A61B 5/0042; A61B 5/055; G01R 33/56366; G01R 33/5607;
(Continued)

(56) References Cited

U.S. PATENT DOCUMENTS

| 2013/0096418 A1 | 4/2013 | Jung |
| 2013/0265047 A1 | 10/2013 | Griwold et al. |

(Continued)

OTHER PUBLICATIONS

Ma et al "Magnetic Resonance Fingerprinting" Nature, vol. 495, p. 187-193.

(Continued)

*Primary Examiner* — Carolyn A Pehlke (57) ABSTRACT

The invention provides for a method of operating a magnetic resonance imaging system for imaging a subject. The method comprises acquiring (700) tagged magnetic resonance data (642) and a first portion (644) of fingerprinting magnetic resonance data by controlling the magnetic resonance imaging system with tagging pulse sequence commands (100). The tagging pulse sequence commands comprise a tagging inversion pulse portion (102) for spin labeling a tagging location within the subject. The tagging pulse sequence commands comprise a background suppression portion (104). The background suppression portion comprises MRF pulse sequence commands for acquiring fingerprinting magnetic resonance data according to a magnetic resonance fingerprinting protocol. The tagging pulse sequence commands comprise an image acquisition portion (106). The method comprises acquiring (702) control mag-
(Continued)

netic resonance data (646) and a second portion (648) of the fingerprinting magnetic resonance data by controlling the magnetic resonance imaging system with control pulse sequence commands. The control pulse sequence commands comprise a control inversion pulse portion (202). The control pulse sequence commands comprise the background suppression portion (104'). The control pulse sequence commands comprise the image acquisition portion (106). The method comprises reconstructing (704) tagged magnitude images (650) using the tagged magnetic resonance data. The method comprises reconstructing (706) a control magnitude images (652) using the control magnetic resonance data. The method comprises constructing (708) an ASL image by subtracting the control magnitude images and the tagged magnitude images from each other. The method comprises reconstructing (710) a series of magnetic resonance fingerprinting images (656) using the first portion of the fingerprinting magnetic resonance data and/or the second portion of the fingerprinting magnetic resonance data. The method comprises generating (712) at least one magnetic resonance parametric map (658) by comparing the series of magnetic resonance fingerprinting images with a magnetic resonance fingerprinting dictionary.

15 Claims, 4 Drawing Sheets

(51) Int. Cl.
| | | |
|---|---|---|
| | *A61B 5/055* | (2006.01) |
| | *A61B 5/026* | (2006.01) |
| | *G01R 33/56* | (2006.01) |
| | *G06T 7/00* | (2017.01) |
| | *G01R 33/561* | (2006.01) |

(52) U.S. Cl.
CPC .......... *A61B 5/055* (2013.01); *G01R 33/5607* (2013.01); *G01R 33/5608* (2013.01); *G01R 33/56366* (2013.01); *G06T 7/0012* (2013.01); *G01R 33/5616* (2013.01); *G06T 2207/10088* (2013.01); *G06T 2207/30004* (2013.01)

(58) Field of Classification Search
CPC ............ G01R 33/5608; G01R 33/5635; G01R 33/5616; G01R 33/4838; G01R 33/4824
See application file for complete search history.

(56) References Cited

U.S. PATENT DOCUMENTS

| | | |
|---|---|---|
| 2013/0271132 A1 | 10/2013 | Griswold |
| 2015/0272453 A1 | 10/2015 | Heberlein et al. |
| 2015/0297101 A1 | 10/2015 | Hernandez-Garcia |
| 2016/0025835 A1 | 1/2016 | Gulani et al. |

OTHER PUBLICATIONS

Bernstein et al "Handbook of MRI Pulse Sequences" p. 802-829 2004.
Wright et al "Theoretical Framework for MR Fingerprinting With ASL . . . " Proceedings of the International Soc. for Magnetic Reson. in Med., vol. 22, p. 417, May 2014.
Alsop et al "Recommended Implementation of Arterial Spin-Labeled Perfusion MRI for Clinical Applicaitons . . . " Magn. Reson. in Med. vol. 73, No. 1 Apr. 8, 2014 p. 102-116.
Petcharunpaisan et al "Arterial Spin Lableing in Neuroimaging" World Journal of Radiology, vol. 2, No. 10, Oct. 28, 2010.
Y. Jiang et al., "MR Fingerprinting Using Fast Imaging with Steady State Precession with Spiral Readout" Magn Reson Med 74:1621-1631 (2015).
R. B. Buxton et al., "A general kinetic model for quantitative perfusion imaging with arterial spin labeling" Magn Reson Med 40:383-396 (1998).
K. Wright et al., "Theoretical Framework for MR Fingerprinting with ASL" Proc Intl Soc Mag Reson Med 22, No. 0417 (2014).
P. Su et al., "Arterial Spin Labeling without Control Label Printing and Post-Labeling Delay" Proc Intl Soc Mag Reson Med 23, No. 0276 (2015).
D. Garcia et al., "Efficiency of Inversion Pulses for Background Suppressed Arterial Spin Labeling" Magn Reson Med 54:366-372 (2005).
Y. Suzuki et al., "Simultaneous Acquisition of Perfusion Maps . . . " Proc Intl Soc Mag Reson Med 22, No. 0720 (2014).
Hamilton et al "MR Fingerprinting for Rapid Quantificaiton of Myocardial T1, T2, and Proton Spin Density" Magnetic Reson. in Med. 2016.

FIG. 6

COMBINED ARTERIAL SPIN LABELING AND MAGNETIC RESONANCE FINGERPRINTING

CROSS REFERENCE TO RELATED APPLICATIONS

This application is a U.S. national phase application of International Application No. PCT/EP2017/075614 filed on Oct. 9, 2017, which claims the benefit of EP Application Serial No. 16192733.0 filed on Oct. 7, 2016 and is incorporated herein by reference.

FIELD OF THE INVENTION

The invention relates to magnetic resonance imaging, in particular to both arterial spin labeling and magnetic resonance fingerprinting.

BACKGROUND OF THE INVENTION

Magnetic Resonance fingerprinting (MRF) is a technique where a number of RF pulses often associated with appropriate gradient switching, distributed in time, are applied such that they cause signals from different materials or tissues to have a unique contribution to the measured Magnetic Resonance (MR) signal. A dictionary of precalculated signal contributions from a large set or a fixed number of substances is compared to the measured MR signals within each single voxel. Furthermore, also the composition within each voxel can further be determined. For example if it is known that a voxel only contains gray matter, white matter, CSF, or fat the contribution from these three materials need only be considered to accurately determine the composition of the voxel. If a larger dictionary with higher resolution is used, MR fingerprinting can be used to determine different tissue parameters of a voxel (such as T1, T2, . . . ) simultaneously and quantitatively.

The magnetic resonance fingerprinting technique was introduced in the journal article Ma et al., "Magnetic Resonance Fingerprinting," Nature, Vol. 495, pp. 187 to 193, doi:10.1038/nature11971. The magnetic fingerprinting technique is also described in United States patent applications US 2013/0271132 A1 and US 2013/0265047 A1. A large static magnetic field is used by Magnetic Resonance Imaging (MRI) scanners to align the nuclear spins of atoms as part of the procedure for producing images within the body of a patient. This large static magnetic field is referred to as the B0 field.

During an MRI scan, Radio Frequency (RF) pulses generated by one or more transmitter coils cause a called B1 field. Additionally applied gradient fields and the B1 field cause perturbations to the effective local magnetic field. RF signals are then emitted by the nuclear spins and detected by one or more receiver coils. These RF signals are used to construct the MR images. These coils can also be referred to as antennas.

MRI scanners are able to construct images of either slices or volumes. A slice is a thin volume that is only one voxel thick. A voxel is a small volume element over which the MR signal is averaged, and represents the resolution of the MR image. A voxel may also be referred to as a pixel (picture element) herein if a single slice is considered.

By performing different magnetic resonance imaging protocols (which are implemented as pulse sequences or pulse sequence commands), different types of information can be measured about a subject. For example, there are various techniques, which enable the encoding of spins such that the flow or diffusion of fluid can be directly measured. Arterial spin tagging is a technique where the spins of blood passing through a group of arteries or even single arteries can be magnetically labeled and then imaged. The reference book "Handbook of MRI Pulse Sequences" (hereafter "Handbook of MRI Pulse Sequences") by Bernstein et. al., Elsevier, 2004, ISBN 978-0-12-092861-3 describes in section 17.1 (pp. 802 through 829) provides a review of several different arterial spin tagging techniques.

SUMMARY OF THE INVENTION

The invention provides for a Magnetic Resonance (MR) imaging system, a computer program product, and a method in the independent claims. Embodiments are given in the dependent claims.

During Arterial Spin Labeling (ASL) magnetic resonance imaging, a bolus of blood water protons within a tagging location is magnetically labeled. Typically there is a delay to allow the bolus to travel to or through a region of interest. To better image the tagged blood as it flows through a region of interest, background suppression is performed on the region of interest during the delay. After the delay magnetic resonance data is acquired. Embodiments expand the amount and type of data available during an ASL MR protocol by performing a magnetic resonance fingerprinting imaging protocol during the delay (and background suppression). Comparatively small flip angles (smaller than is used for the background suppression) can be used for the magnetic resonance fingerprinting protocol such that the effect of performing the magnetic resonance fingerprinting has a negligible effect on the background suppression. The addition of the magnetic resonance fingerprinting may possibly not result in any increase in the time needed to perform the ASL imaging protocol.

In addition to providing additional information, some embodiments may also use the results of the ASL to improve the quality of the MR fingerprinting. For example the ASL protocol may be used to generate a cerebral blood flow map. When analyzing a particular voxel using MRF, the cerebral blood flow map may be used to determine a blood flow value for the particular voxel. The MR fingerprinting dictionary may be customized to particular blood flow values and/or ranges of blood flow values. This may results in more accurate MRF.

The Nature article by Ma et al. introduces the basic idea of magnetic resonance fingerprinting and terminology which is used to describe this technique such as the dictionary, which is referred to herein as a "steady state magnetic resonance fingerprinting dictionary" or a "transient resonance fingerprinting dictionary." The term "dictionary" alone is understood to refer to a magnetic resonance fingerprinting dictionary.

In one aspect, the invention provides for a magnetic resonance imaging system for imaging a subject. The magnetic resonance imaging system comprises a memory for storing machine-executable instructions. The memory further contains tagging pulse sequence commands and control pulse sequence commands. Pulse sequence commands as used herein encompass commands or data that may be converted or compiled into commands that are used to control a magnetic resonance imaging system to acquire magnetic resonance data. The terms tagging and control with reference to the pulse sequence commands are used as labels to differentiate two distinct sets of pulse sequence commands.

The tagging pulse sequence commands and the control pulse sequence commands are used for arterial spin tagging as is described in section 17.1 of the Handbook of MRI Pulse Sequences. The tagging inversion pulse portion is used to label a bolus of blood that is travelling through one or more arteries. The tagging inversion pulse portion results in a magnetization transfer effect in the imaging volume that will be visible in a magnitude image calculated from magnetic resonance data that is acquired using the tagging pulse sequence commands. The control inversion pulse portion is constructed so that it causes a magnetization transfer effect that is equivalent or nearly equivalent to the magnetization transfer effect caused by the tagging inversion pulse portion.

The tagging pulse sequence commands comprise a tagging inversion pulse portion for spin labeling a tagging location within the subject. The tagging pulse sequence commands comprise a background suppression portion. The background suppression portion comprises magnetic resonance fingerprinting pulse sequence commands for acquiring fingerprinting magnetic resonance data according to a magnetic resonance fingerprinting protocol. The tagging pulse sequence commands comprise an image acquisition portion. The tagging pulse sequence commands and the control pulse sequence commands are used to acquire magnetic resonance data for and also to construct arterial spin labeling images. The control pulse sequence commands comprise a control inversion pulse portion.

The control pulse sequence commands comprise the background suppression portion. The control pulse sequence commands comprise the image acquisition portion. The tagging pulse sequence commands and the control pulse sequence commands are used to acquire magnetic resonance data that is used for constructing an ASL or arterial spin labeling image using standard techniques. However, the background suppression portion is modified in that there are additional magnetic resonance fingerprinting pulse sequence commands that are added to this portion. This enables magnetic resonance fingerprinting to be performed at the same time that the arterial spin labeling is performed.

The tagging inversion pulse portion and the control inversion pulse portion may be performed before the background suppression portion. The background suppression portion may be performed before the image acquisition portion.

The magnetic resonance imaging system further comprises a processor for controlling the magnetic resonance imaging system. Execution of the machine-executable instructions causes the processor to acquire tagged magnetic resonance data and a first portion of the fingerprinting magnetic resonance data by controlling the magnetic resonance imaging system with the tagging pulse sequence commands. The first portion of the fingerprinting magnetic resonance data is acquired when the background suppression portion is executed. The tagged magnetic resonance data is acquired when the image acquisition portion of the tagging pulse sequence commands are executed.

Execution of the machine-executable instructions further cause the processor to acquire control magnetic resonance data and a second portion of the fingerprinting magnetic resonance data by controlling the magnetic resonance imaging system with the control pulse sequence commands. The control magnetic resonance data is acquired when the image acquisition portion of the tagging pulse sequence commands is executed. The second portion of the fingerprinting magnetic resonance data is acquired when the background suppression portion of the tagging pulse sequence commands is executed. The tagged magnetic resonance data and the control magnetic resonance data represent the data that is normally acquired in conventional arterial spin labeling protocols. The first portion of the fingerprinting magnetic resonance data and the second portion of the fingerprinting magnetic resonance data represent the data that is additionally acquired by adding the magnetic resonance fingerprinting pulse sequence commands to the background suppression portion. Execution of the machine-executable instructions further cause the processor to reconstruct a tagged magnitude image using the tagged magnetic resonance data.

Execution of the machine-executable instructions further cause the processor to reconstruct a control magnitude image using the control magnetic resonance data. Execution of the machine-executable instructions further cause the processor to construct an ASL or arterial spin labeling image by subtracting the control magnitude image and the tagged magnitude image from each other.

Execution of the machine-executable instructions further cause the processor to reconstruct a series of magnetic resonance fingerprinting images using the first portion of the fingerprinting magnetic resonance data and/or the second portion of the fingerprinting magnetic resonance data. In magnetic resonance fingerprinting a series of images are constructed. The values for a particular voxel throughout the entire series is then compared to a dictionary to infer either the material properties or intrinsic properties of that particular voxel. For example, the fractions of white or gray matter could be examined within a particular voxel. Or other values such as the various relaxation times or other properties. In reconstructing the series of magnetic resonance fingerprinting images there are a variety of ways in which the first portion of the fingerprinting magnetic resonance data and the second portion of the fingerprinting magnetic resonance data could be used. For example if the magnetic resonance fingerprinting pulse sequence commands are identical within both the first portion and the second portion of the fingerprinting magnetic resonance data the two might be averaged.

In other examples, the k-space which is sampled by the two portions may be slightly different. In this case the k-space data for corresponding acquisitions may be combined. In other examples the k-space sampling may also be different and the first portion is used to construct a first part of the series of the images and the second portion is used to construct a second portion of the magnetic resonance fingerprinting images. This results in a larger series of images that would be present if just the first portion or the second portion is used. In other examples the series of magnetic resonance fingerprinting images may be used by using just one of the first portion or the second portion of the fingerprinting magnetic resonance data. There are therefore a variety of different ways in which the first portion of the fingerprinting magnetic resonance data and the second portion of the fingerprinting magnetic resonance data may be used.

Execution of the machine-executable instructions further cause the processor to generate at least one magnetic resonance parametric map by comparing the series of magnetic resonance fingerprinting images with a magnetic resonance fingerprinting dictionary. The parametric map may for instance be a two-dimensional or three-dimensional mapping of some intrinsic parameter. This may for instance be the concentration of some compound, the fat fraction or a physical property such as the T1, T2 or other value. In some examples the magnetic resonance parametric map may be combined with the ASL image to generate a composite image that displays not only data from the arterial spin labeling but also the additional information contained in the at least one magnetic resonance parametric map.

This embodiment may be beneficial because it enables the acquisition of not only arterial spin labeling images but also magnetic resonance parametric maps at the same time. This may provide for better diagnostic information for a health practitioner. It may also acquire or provide for a more accurate correlation of arterial spin labeling images with data derived from magnetic resonance fingerprinting. It may also accelerate the acquisition of both modalities of data as they are both acquired at the same time. One does not need to be acquired sequentially after the other and then later registered to the other image.

In another embodiment, the background suppression portion further comprises background suppression pulse sequence commands. The background suppression pulse sequence commands are commands which are used to form background suppression as is typical in an arterial spin labeling imaging protocol.

The background suppression pulse sequence commands use what may be described as typically a large flip angle. The flip angle is for instance typically above 150° to approximately 180°. These are used to perform background suppression in arterial spin labeling protocols.

In another embodiment, the background suppression portion is discretely divided into regions of the background suppression pulse sequence commands and at least one region of the magnetic resonance pulse sequence commands. In some cases the background suppression pulse sequence commands are not used during the magnetic resonance fingerprinting. For example varying the flip angle of the magnetic resonance fingerprinting pulse sequence commands smoothly from one pulse repetition to the next may have a benefit in providing magnetic resonance fingerprinting data that is able to be more accurately represented in the magnetic resonance fingerprinting dictionary.

In another embodiment, the background suppression pulse sequence commands are incorporated into the magnetic resonance fingerprinting pulse sequence commands. The relatively large flip angles of the background suppression pulse sequence commands are then used additionally with magnetic resonance fingerprinting pulse sequence commands with relatively or comparatively low flip angles. This may have the benefit of providing for more data which is useful for the magnetic resonance fingerprinting technique. The encoding of the T1 or T2 values in the background suppression pulse sequence commands may result in more accurate measurement of the T1 or T2 values.

In another embodiment, the tagging pulse sequence commands and control pulse sequence commands comprise a delay between the last of the at least one region of the magnetic resonance fingerprinting pulse sequence commands and the image acquisition portion. In this case the magnetic resonance fingerprinting is stopped or there is a delay prior to the image acquisition portion of the arterial spin labeling. This may have the effect of reducing any effect of the magnetic resonance fingerprinting on the acquisition of the arterial spin labeling magnetic resonance data.

In another embodiment, the magnetic resonance fingerprinting pulse sequence commands comprise a flip angle portion.

In another embodiment, the flip angle portion in the MRF pulse sequence commands of the tagging pulse sequence commands and the MRF pulse sequence commands of the control pulse sequence commands are identical. This may have the benefit of providing for a tagged magnetic resonance image and a control magnetic resonance image which reconstruct a higher quality ASL image. In some examples the flip angle portions are identical but the gradients may be modified such that the k-space data acquired in the first portion and the second portion of the magnetic resonance fingerprinting data are different or are interleaved.

In another embodiment, the flip angle portion is configured for generating flip angles below any one of the following: 10°, 8°, 7°, 6° and 5°. The use of flip angles below these values may be beneficial because it may reduce the chances that the magnetic resonance fingerprinting affects the background suppression.

In another embodiment, the at least one magnetic resonance parametric map comprises angiography data. The angiography data comprises images that show the vessel anatomy of the subject.

In another embodiment, the MRF pulse sequence commands of the tagging pulse sequence commands comprise a first gradient encoding portion. The MRF pulse sequence commands of the control pulse sequence commands comprise a second gradient encoding portion. The first gradient encoding portion and the second gradient encoding portion encode identical portions of k-space. This embodiment may be beneficial because the background suppression portion of the tagging pulse sequence commands and the control pulse sequence commands are identical. This may lead to more reproducible results. Another potential advantage is that the samples of k-space acquired with the first portion of the fingerprinting magnetic resonance data may be combined or averaged with the second portion of the fingerprinting magnetic resonance data. This may lead to a reduction in noise artifacts.

In another embodiment, execution of the machine-executable instructions further cause the processor to calculate average magnetic resonance data by averaging corresponding elements of the first portion of the fingerprinting magnetic resonance data with the second portion of the fingerprinting magnetic resonance data. The series of magnetic resonance fingerprinting images may be reconstructed using the averaged magnetic resonance data. The averaging of the first and second portions of the fingerprinting magnetic resonance data may result in reduced amounts of noise or noise artifacts in the series of magnetic resonance fingerprinting images.

In another embodiment, the MRF pulse sequence commands of the tagging pulse sequence commands comprise a first gradient encoding portion. The MRF pulse sequence commands of the control pulse sequence commands comprise a second gradient encoding portion. The first gradient encoding portion and the second gradient encoding portion encode interleaving portions of k-space. This embodiment may be beneficial because it may provide for increased sampling of k-space which may result in improved image quality.

In another embodiment, the first gradient encoding portion encodes the first portion of the fingerprinting magnetic resonance data using an encoding modality according to any one of the following: spirally in k-space, radially in k-space, and in cartesian k-space. The second gradient encoding portion encodes the second portion of the fingerprinting magnetic resonance data using the encoding modality. This embodiment describes several ways in which the first and second portion of the fingerprinting magnetic resonance data can be encoded when the first gradient encoding portion and the second gradient encoding portion encode interleaving portions of k-space.

In another embodiment, execution of the tagging inversion pulse portion by the magnetic resonance imaging system causes a tagging magnetization transfer effect in tagged magnitude images. Execution of the control inversion pulse portion by the magnetic resonance imaging system causes a control magnetization transfer effect in control magnitude images. The tagging magnetization transfer effect is subtracted out of the arterial image by the control magnetization transfer effect.

In another embodiment, the ASL image comprises a cerebral blood flow map. The magnetic resonance fingerprinting dictionary is a function of cerebral blood flow.

Execution of the machine-executable instructions cause the processor to use the cerebral blood flow map to provide the cerebral blood flow to the magnetic resonance fingerprinting dictionary during determination of the at least one magnetic resonance parametric map. The cerebral blood flow map may be used to get a per pixel value of the cerebral blood flow which is then used as a value as input to the magnetic resonance fingerprinting dictionary. The magnetic resonance fingerprinting dictionary can therefore be pre-calculated as a function of the cerebral blood flow. This may provide for improved magnetic resonance fingerprinting during arterial spin labeling imaging.

In another embodiment, the magnetic resonance parametric map comprises any one of the following: a T2 map, a T1 map, a Mean Transit Time (MTT) map, and combinations thereof. An MTT map is defined as a spatially dependent mapping of the length of the time a certain volume of blood spins in the cerebral capillary circulation.

In another aspect, the invention provides for a computer program product comprising machine-executable instructions for execution by a processor controlling the magnetic resonance imaging system. Execution of the machine-executable instructions causes the processor to acquire tagged magnetic resonance data and a first portion of the fingerprinting magnetic resonance data by controlling the magnetic resonance imaging system with tagging pulse sequence commands. The tagging pulse sequence commands comprise a tagging inversion pulse portion for spin labeling a tagging location within the subject. The tagging pulse sequence commands comprise a background suppression portion. The background suppression portion comprises MRF pulse sequence commands for acquiring fingerprinting magnetic resonance data according to the magnetic resonance fingerprinting protocol.

The tagging pulse sequence commands comprise an image acquisition portion. Execution of the machine-executable instructions further cause the processor to acquire control magnetic resonance data and a second portion of the fingerprinting magnetic resonance data by controlling the magnetic resonance imaging system with control pulse sequence commands. The control pulse sequence commands comprise a control inversion pulse portion. The control pulse sequence commands comprise the background suppression portion. The control pulse sequence commands comprise the image acquisition portion. Execution of the machine-executable instructions further cause the processor to reconstruct tagged magnitude images using the tagged magnetic resonance data. Execution of the machine-executable instructions further cause the processor to reconstruct control magnitude images using the control magnetic resonance data. Execution of the machine-executable instructions further cause the processor to construct an ASL image by subtracting the control magnitude images and the tagged magnitude images from each other.

Execution of the machine-executable instructions further cause the processor to reconstruct a series of magnetic resonance fingerprinting images using the first portion of the fingerprinting magnetic resonance data and/or the second portion of the fingerprinting magnetic resonance data. Execution of the machine-executable instructions further cause the processor to generate at least one magnetic resonance parametric map by comparing the series of magnetic resonance fingerprinting images with a magnetic resonance fingerprinting dictionary.

In another aspect, the invention provides for a method of operating a magnetic resonance imaging system for imaging a subject. The method comprises acquiring tagged magnetic resonance data and a first portion of the fingerprinting magnetic resonance data by controlling the magnetic resonance imaging system with tagging pulse sequence commands. The tagging pulse sequence commands comprise a tagging inversion pulse portion for spin labeling a tagging location within the subject. The tagging pulse sequence commands comprise a background suppression portion. The background suppression portion comprises MRF pulse sequence commands for acquiring fingerprinting magnetic resonance data according to a magnetic resonance fingerprinting protocol. The tagging pulse sequence commands comprise an image acquisition portion.

The method further comprises acquiring control magnetic resonance data and a second portion of the fingerprinting magnetic resonance data by controlling the magnetic resonance imaging system with control pulse sequence commands. The control pulse sequence commands comprise a control inversion pulse portion. The control pulse sequence commands comprise a background suppression portion. The control pulse sequence commands comprise the image acquisition portion. The method further comprises reconstructing tagged magnitude images using the tagged magnetic resonance data. The method further comprises reconstructing control magnitude images using the control magnetic resonance data.

The method further comprises constructing an ASL image by subtracting the control magnitude images and the tagged magnitude images from each other. The control magnitude images and the tagged magnitude images are produced as pairs of a single control magnitude image and a single tagged magnitude image. The corresponding pair: a single control magnitude image and a single tagged magnitude image are subtracted from each other. The ASL image is then constructed by summing or averaging many of these pairs of images. Alternatively, the control magnitude images can be averaged or summed to form an average control magnitude image and the tagged magnitude images can be averaged or summed to form an average tagged magnitude image. In this alternative the ASL image can then be constructed by subtracting the average control magnitude image and the average tagged magnitude image.

The method further comprises reconstructing a series of magnetic resonance fingerprinting images using the first portion of the fingerprinting magnetic resonance data and/or the second portion of the fingerprinting magnetic resonance data. The method further comprises generating at least one magnetic resonance parametric map by comparing the series of magnetic resonance fingerprinting images with a magnetic resonance fingerprinting dictionary.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit,"

"module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical imaging data. A Magnetic Resonance (MR) image is defined herein as being the reconstructed two or three dimensional visualization of anatomic data contained within the magnetic resonance imaging data.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these figures are either equivalent elements or perform the same function. Elements which have been discussed previously will not necessarily be discussed in later figures if the function is equivalent.

Magnetic Resonance Fingerprinting (MRF) is a promising technique for time-efficient quantification of tissue parameters such as T1 and T2. By exposing the tissue of interest to a train of RF pulses that induce varying flip angles (FAs) with respect to a main magnetic field, a characteristic signal or 'fingerprint' is obtained for each voxel. These fingerprints can then be compared to a dictionary of all possible signal evolutions, which yields the tissue parameters of each voxel.

Examples may extend MRF to include perfusion information by combination with the arterial spin labeling (ASL) technique. In ASL, the blood water protons in the large arteries of the head and neck are labeled by magnetic inversion, and after a delay of 1-2 s, which is required for the labeled blood to flow into the imaging region, the signals in the brain tissue are acquired. By repeating the experiment without labeling, the so-called control image is acquired. Subtraction of labeled and control image yields a perfusion-weighted image. Using physiological models such as the general kinetic model, quantitative information such as Cerebral Blood Flow (CBF) can be obtained. To reduce the dynamic range of this subtraction in most ASL protocols appropriate background suppression pulses are applied for both labeled and control image.

In conventional ASL techniques, the post-labeling delay is an idle time, i.e. the scanner does not encode or acquire data. The overall scan time of these techniques could potentially be used more efficiently to acquire additional information.

In previously proposed approaches to combine ASL and MRF, absence of inversion pulses for the tissue spin system impeded efficient encoding of relaxation parameters. Overall, the accuracy of the T1, CBF, and mean arterial transit time (MTT) matching appeared limited. Furthermore, variation of the labeling duration may result in not fully predictable labeling conditions due to patient dependent arterial flow velocities.

Examples may provide for a combined ASL-MRF sequence consists of an interleaved combination of conventional ASL and a varying low-FA pattern that is employed to quantify T1 and T2 parameters, leaving the basic ASL sequence almost unchanged.

The conventionally used background suppression pulses are replaced or extended by a train of RF pulses with varying low flip angles. This makes it possible to achieve background suppression of the static tissue in the imaging volume and at the same time to encode the voxels for subsequent MRF analysis.

Since the structure of the ASL labeling and data acquisition is left practically unaltered, analysis of the ASL data can be performed using standard methods, which yields a CBF map of the examined tissue. Using this data as a priori information, the MRF data is then analyzed to obtain maps of T1, T2, and MTT.

An example of an ASL-MRF sequence is depicted below in FIGS. 1 and 2. In the initial phase (tagging inversion portion 102 or control inversion pulse portion 202), a conventional labeling, for example pCASL; is performed distal to the volume of interest (VOI) or region of interest 109 to invert the blood water spins in the major feeding vessels of the brain. In the delay time between this labeling and the acquisition of the ASL data, the tissue of interest is subjected to a train of RF pulses with varying FAs, similar to previous implementations of MRF. Several inversion pulses are included to facilitate background suppression of stationary tissue spins in the following ASL acquisition. In addition, these inversion pulses considerably improve the encoding of the relaxation parameters in the MRF data. To avoid saturation of inflowing labeled (inverted) blood water spins due to the RF pulse train, only low FAs are employed.

Figure 1:
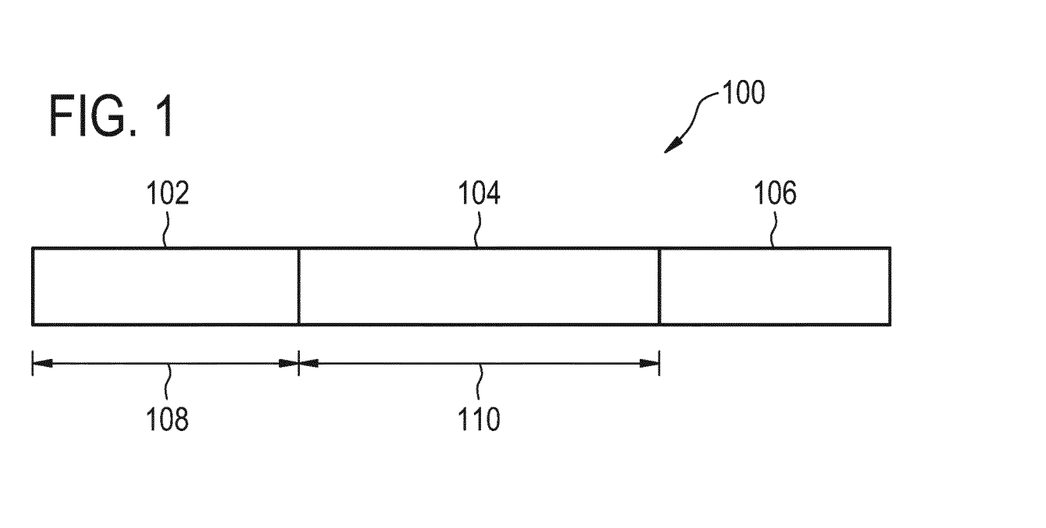
FIG. 1 illustrates an example of tagging pulse sequence commands.

FIG. 1 illustrates an example of tagging pulse sequence commands 100. The tagging pulse sequence commands comprise a tagging inversion pulse portion 102 that is followed by a background suppression portion 104. The background suppression portion 104 is followed by an image acquisition portion 106. The pulse sequence 100 represented in FIG. 1 is similar to a conventional ASL or arterial spin labeling pulse sequence except that during the background suppression portion 104 additional low flip angle radio-frequency pulses and data acquisition is acquired such that magnetic resonance fingerprinting is performed during the background suppression portion 104. During the tagging inversion pulse portion 102 a region is tagged as is commonly performed in conventional arterial spin labeling magnetic resonance imaging protocols. Likewise, during the image acquisition portion 106 the tagged magnetic resonance data is acquired that is used for producing the arterial spin labeled image. The tagging inversion pulse portion 102 lasts for a labeling duration 108 (in this example 1290 ms). There is then a post-labeling delay 110 (in this example 1710 ms) before the tagged magnetic resonance data is acquired during the image acquisition portion 106. During the post-labeling delay 110 the background suppression may be performed and also magnetic resonance fingerprinting data acquisition. Both of these steps are combined in the background suppression portion 104.

Figure 2:
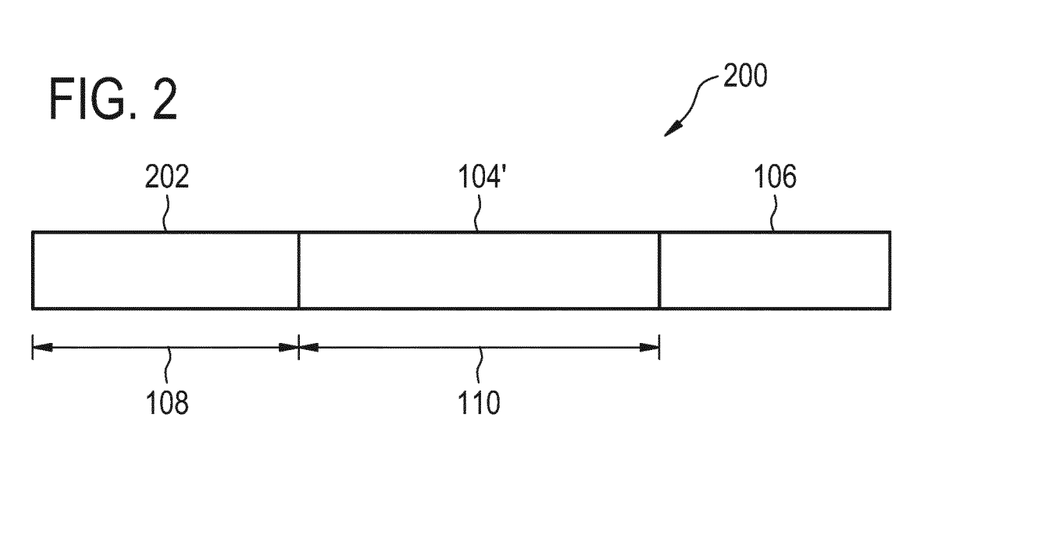
FIG. 2 illustrates an example of control pulse sequence commands.

FIG. 2 illustrates an example of a set of control pulse sequence commands 200. The control pulse sequence commands 200 are similar to the tagging pulse sequence commands 100 illustrated in FIG. 1. In this case the tagging inversion pulse portion 102 is replaced with a control inversion pulse portion 202. During the control inversion portion 202 there is no actual labeling of spins. The control inversion portion 202 is designed as is typical in conventional arterial spin labeling protocols. The control inversion portion 202 is designed such that it causes a magnetization transfer effect that is comparable to the magnetization transfer effect that is caused by the tagging inversion pulse portion 102. This enables the magnetization transfer effect in the resulting arterial spin label image to be subtracted out.

The background suppression portion 104' of FIG. 2 may be identical with the background suppression portion 104 illustrated in FIG. 1. In other cases the background suppression portion 104' may have minor differences such as the gradients during the sampling of the magnetic resonance fingerprinting data may have slightly different gradients such that the k-space data that is acquired is acquired from different points. This may allow the data acquired during the background suppression portion 104 and the background suppression portion 104' to be interleaved.

Figure 3:
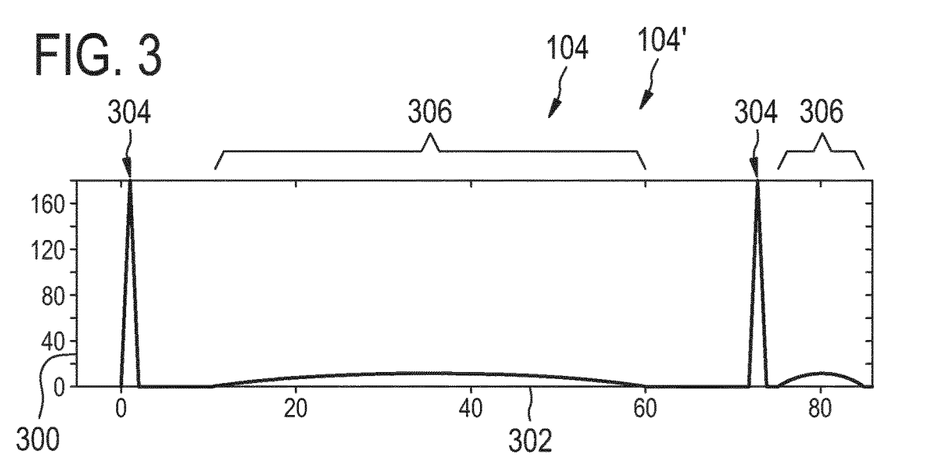
FIG. 3 illustrates an example of the amplitude of RF pulses for multiple repetition pulses for the background suppression portion.
Figure 4:
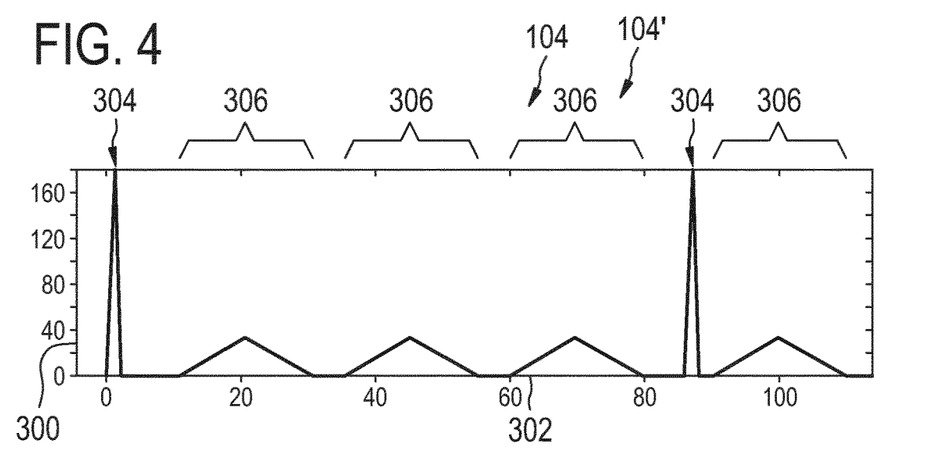
FIG. 4 illustrates a further example of the amplitude of RF pulses for multiple repetition pulses for the background suppression portion.
Figure 5:
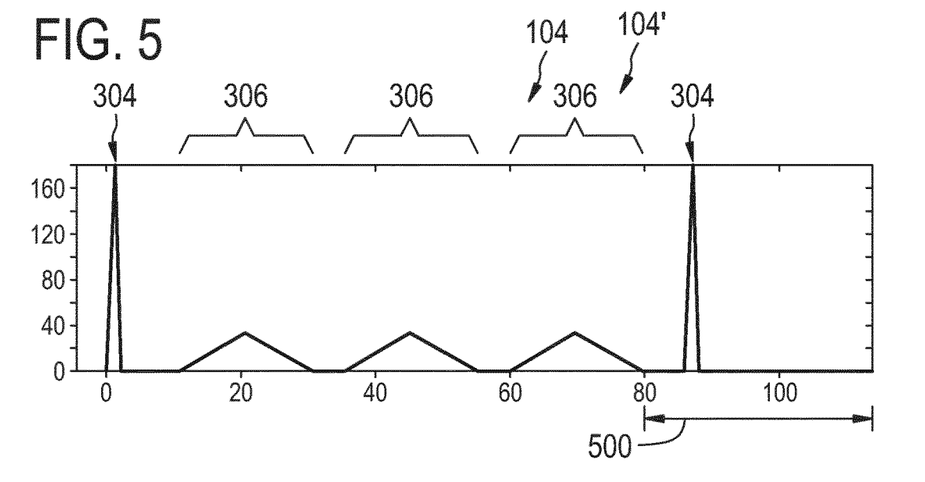
FIG. 5 illustrates a further example of the amplitude of RF pulses for multiple repetition pulses for the background suppression portion.

FIGS. 3 through 5 below depicts two example patterns that realize efficient suppression of tissue signals as well as sufficient encoding of relaxation parameters.

For the ASL and MRF data acquisition, single-shot 2D echo-planar imaging (EPI) or spiral readouts may for example be used. 2D EPI and spiral readouts are most often used for the ASL readout. However for the for the MRF pulse sequence commands, almost any readout is possible, including spiral, cartesian, and radial. To allow for quantitative analysis of the ASL data, control images are acquired by repeating the entire sequence without prior labeling of the blood water spins. To ensure efficient background suppression, the same FA pattern is employed for both label and control images. For example case of a spiral MRF readout, however, two different interleaves can be acquired, hence reducing the resulting overall degree of undersampling. This is also possible for other read out schemes. In Cartesian readouts, e. g., different lines in k-space can be acquired and then combined to form the final image.

Analysis of the acquired data consists in a two-step procedure. In a first step, the acquired ASL data are analyzed, for example, using a general kinetic model, yielding quantitative CBF maps of the brain tissue. Using this voxel-wise flow information as a fixed parameter, the MRF data are then analyzed using a dictionary with varying values of T1, T2 and MTT.

FIG. 3 illustrates a portion of the background suppression portion 104, 104'. The gradients are not illustrated. However, the flip angle 300 as a function of pulse repetition 302 is shown. The flip angle 300 is a flip angle which is caused by a particular radio-frequency pulse. The RF pulses in the plot in FIG. 3 can be divided into background suppression pulse sequence commands 304 and MRF pulse sequence commands 306. The background suppression pulse sequence commands 304 are relatively large flip angles (RF pulses that cause the flip angles) that are used for the background suppression as is known in arterial spin labeling. There have been additionally added a number of lower flip angle pulse repetitions. These are labeled 306. The background suppression portion 104, 104' can be designed by starting with a standard ASL background suppression portion. The MRF pulse sequence commands 306 may then be added to the standard background suppression portion. The low flip angle MRF pulse sequence commands 306 may have an effect on the background suppression. The duration between the background suppression pulse sequence commands 304 may be adjusted empirically to account for this effect. It may also be possible to adjust the amplitude or flip angle of the background suppression pulse sequence commands 304 to adapt for this effect also.

In some examples magnetic resonance fingerprinting is only performed using the MRF pulse sequence commands 306. In other examples both the background suppression pulse sequence commands 304 and the MRF pulse sequence commands 306 are used for the magnetic resonance fingerprinting protocol.

FIG. 4 shows an alternative background suppression portion 104, 104'. The background suppression portion 104, 104' shown in FIG. 4 is similar to that shown in FIG. 3. However, the MRF pulse sequence commands 306 have a different pattern of flip angles.

FIG. 5 shows a further example of a background suppression portion 104, 104'. The example shown in FIG. 5 is similar to that shown in FIG. 4. In this example the final MRF pulse sequence commands 306 are absent. This introduces a delay 500 between the last MRF pulse sequence commands 306 and the start of the image acquisition portion 106. In some instances this may be useful in reducing the effect of the MRF pulse sequence commands 306 on the image acquisition for the arterial spin labeling.

In one example, the tagging inversion pulse portion comprises an ASL (PASL) inversion pulse, where a large slab of blood water spins is inverted below the tissue of interest. While exhibiting a lower SNR in the ASL data compared to pCASL, such a scheme leaves more time for the variable FA pattern in the MRF phase before arrival of the labeled blood in the tissue.

In one example, a delay is inserted between the MRF and ASL acquisition phases to avoid saturation of the inflowing labeled blood.

In one example, the FA pattern of the MRF readout is specifically designed to enable the extraction of angiography data. For this purpose, relatively low FAs (e.g. below or equal to 7°) are beneficial.

Figure 6:
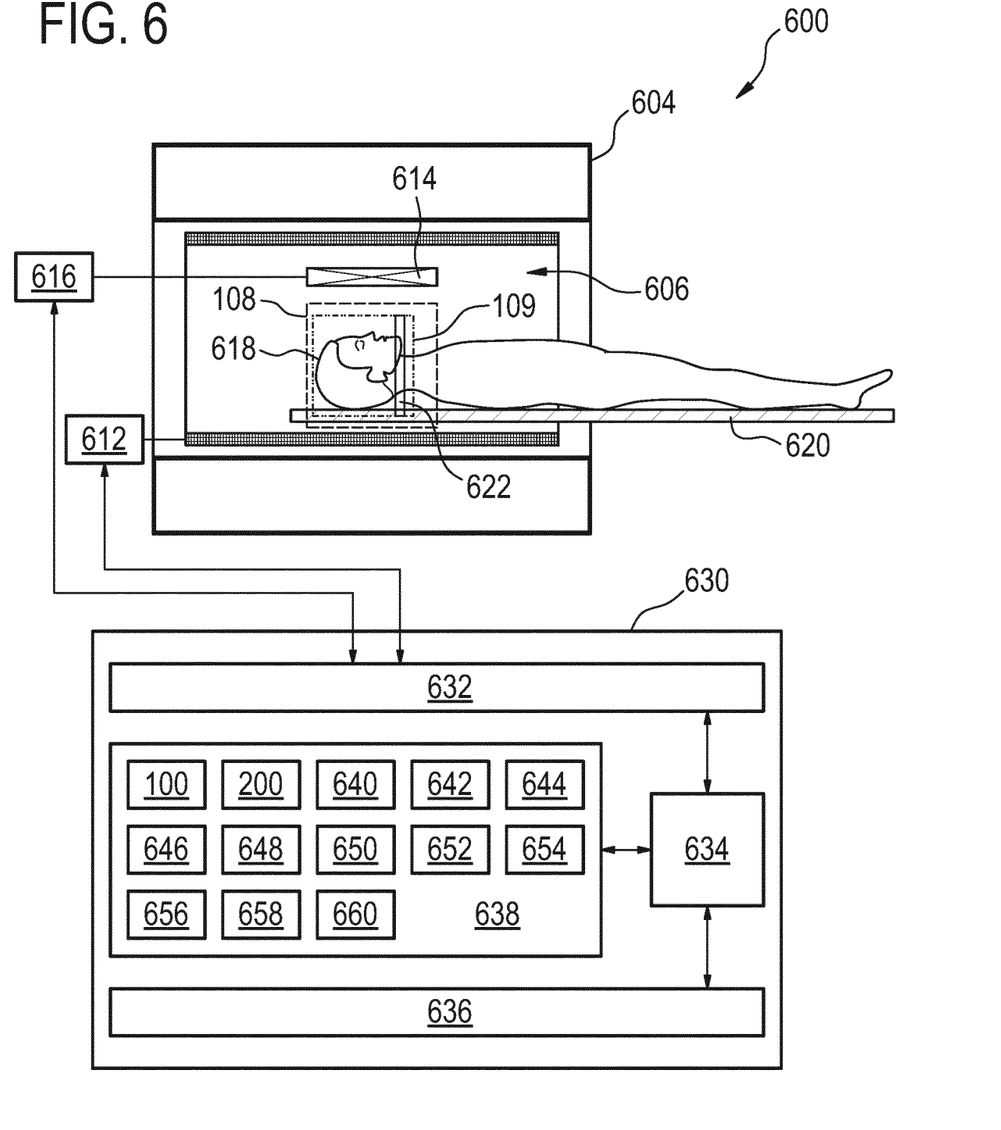
FIG. 6 illustrates an example of a magnetic resonance imaging system.

FIG. 6 shows an example of a magnetic resonance imaging system 500. The magnetic resonance imaging system 500 comprises a magnet 504. The magnet 504 is a superconducting cylindrical type magnet 504 with a bore 506 through it. The use of different types of magnets is also possible. Inside the cryostat of the cylindrical magnet, there is a collection of superconducting coils. Within the bore 506 of the cylindrical magnets there is an imaging zone 508 where the magnetic field is strong and uniform enough to perform magnetic resonance imaging.

Within the bore 506 of the magnet there is also a set of magnetic field gradient coils 510 which is used for acquisition of magnetic resonance data to spatially encode magnetic spins within the imaging zone 508 of the magnet 504. The magnetic field gradient coils 510 are connected to a magnetic field gradient coil power supply 512. The magnetic field gradient coils 510 are intended to be representative. Typically magnetic field gradient coils 510 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Adjacent to the imaging zone 508 is a radio-frequency coil 514 for manipulating the orientation of magnetic spins within the imaging zone 508 and for receiving radio transmissions from spins also within the imaging zone 508. The radio frequency antenna may contain multiple coil elements. The radio frequency antenna may also be referred to as a channel or antenna. The radio-frequency coil 514 is connected to a radio frequency transceiver 516. The radio-frequency coil 514 and radio frequency transceiver 516 may be replaced by separate transmit and receive coils and a separate transmitter and receiver. It is understood that the radio-frequency coil 514 and the radio frequency transceiver 516 are representative. The radio-frequency coil 514 is intended to also represent a dedicated transmit antenna and a dedicated receive antenna. Likewise the transceiver 516 may also represent a separate transmitter and receiver. The radio-frequency coil 514 may also have multiple receive/transmit elements and the radio frequency transceiver 516 may have multiple receive/transmit channels.

Within the bore 506 of the magnet 504 there is a subject support 520 which supports the subject in the the imaging zone 508. A region of interest 509 can be seen within the imaging zone 508.

The transceiver 616 and the magnetic field gradient coil power supply 612 can be seen as being connected to a hardware interface 632 of computer system 630. The computer system further comprises a processor 634 that is in communication with the hardware interface 632, a memory 638, and a user interface 636. The memory 638 (also referred to as computer memory) may be any combination of memory which is accessible to the processor 634. This may include such things as main memory, cached memory, and also non-volatile memory such as flash RAM, hard drives, or other storage devices. In some examples the memory 634 may be considered to be a non-transitory computer-readable medium. The memory 634 is shown as storing machine-executable instructions 640 which enable the processor 632 to control the operation and function of the magnetic resonance imaging system 600.

Pulse sequence commands as used herein encompass commands or a timing diagram which may be converted into commands which are used to control the functions of the magnetic resonance imaging system 600 as a function of time. Pulse sequence commands are the implementation of the magnetic resonance imaging protocol applied to a particular magnetic resonance imaging system 600.

Within the region of interest 609 there can be seen a tagging location 622. The tagging location is where the tagging inversion pulse portion labels a bolus of blood that passes through the arteries of the subject 618. In this case the region of interest 609 is shown as encompassing the head. The tagging location 622 in this case is a plane. The tagging is therefore non-selective and any blood passing through the plane 622 will be labeled. The positioning of the plane of the tagging location 622 near the neck of the subject 618 essentially means that all blood entering into the brain of the subject 618 will be effectively tagged. The example shown in FIG. 6 shows non-selective tagging.

The computer memory 638 is shown as containing the tagging pulse sequence commands 100 and the background pulse sequence commands 200. The computer memory 638 is shown as further containing machine-executable instructions 640. The machine-executable instructions 640 enable the processor 634 to control the operation and function of the magnetic resonance imaging system 600. The computer memory is further shown as containing tagged magnetic resonance data 642 and a first portion of fingerprinting magnetic resonance data 644 that were acquired when the tagging pulse sequence commands 100 were used to control the magnetic resonance imaging system 600. The computer memory 638 is further shown as containing control magnetic resonance data 646 and a second portion of fingerprinting magnetic resonance data 648 that were acquired when the processor 634 used the background pulse sequence commands 200 to control the magnetic resonance imaging system 600.

The computer memory 638 is further shown as containing a tagged magnitude image 650 that was reconstructed from the tagged magnetic resonance data 642. The computer memory 638 is further shown as containing a control magnitude image 652 that was reconstructed from the control magnetic resonance data 646. The computer memory 638 is further shown as containing an arterial spin label magnetic resonance image 654 that was constructed by subtracting the tagged magnitude image 650 and the control magnitude image 652 from each other. The computer memory 638 is further shown as containing a series of magnetic resonance fingerprinting images 656 that were reconstructed from the first portion of the fingerprinting magnetic resonance data 644 and/or the second portion of the fingerprinting magnetic resonance data 648. The computer memory 638 is further shown as containing a magnetic resonance parametric map 658 that was calculated by comparing the series of magnetic resonance fingerprinting images 656 to a magnetic resonance fingerprinting dictionary 660 that is stored in the computer memory 638. It is not shown in this FIG., but however the memory 638 may also contain a routine or program for calculating the magnetic resonance fingerprinting dictionary 660 using the tagging pulse sequence commands 100 and/or the background pulse sequence commands 200.

Figure 7:
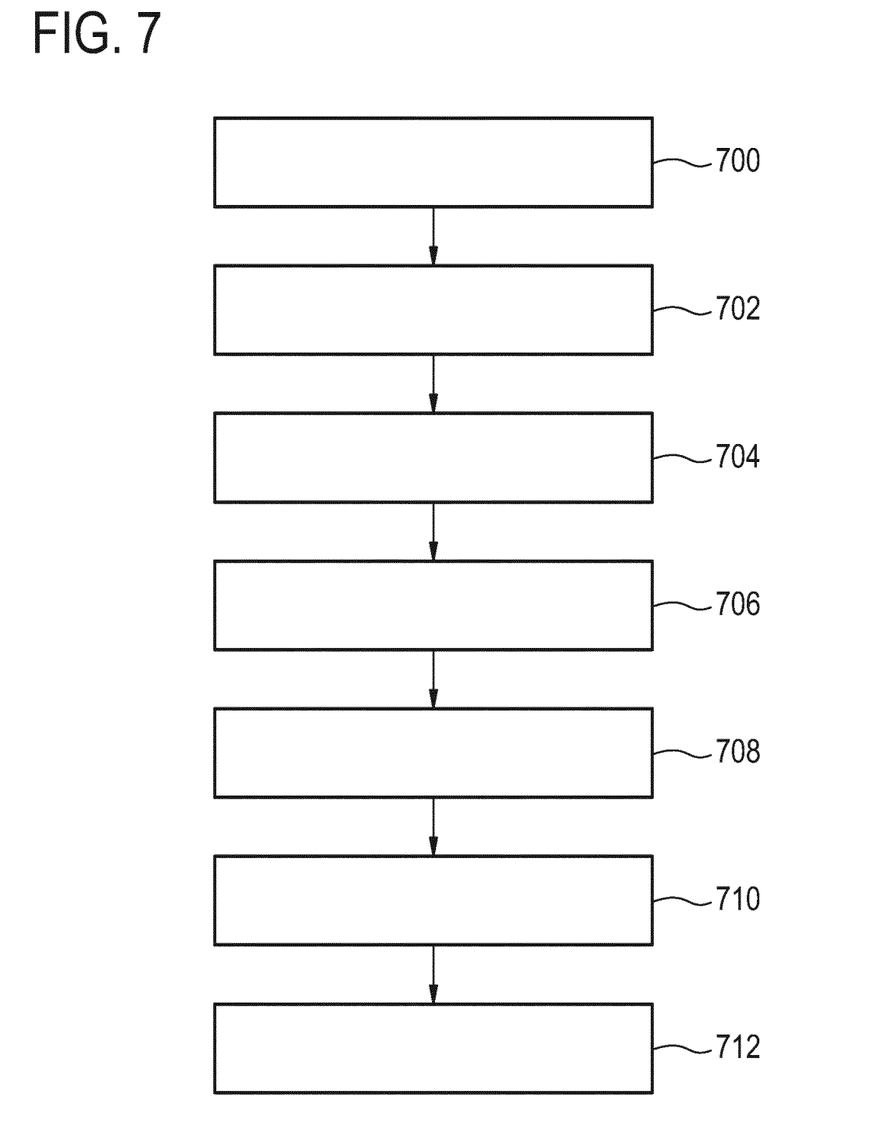
FIG. 7 shows a flow chart which illustrates a method of operating the magnetic resonance imaging system of FIG. 6.

FIG. 7 shows a flowchart which illustrates a method of operating the magnetic resonance imaging system 600 of FIG. 6. First in step 700 tagged magnetic resonance data 642 and a first portion of fingerprinting magnetic resonance data 644 are acquired by controlling the magnetic resonance imaging system with the tagging pulse sequence commands 100. Next in step 602 the control magnetic resonance data 646 and the second portion of the fingerprinting magnetic resonance data 648 is acquired by controlling the magnetic resonance imaging system 600 with the control pulse sequence commands 200. In step 704 a tagged magnitude image 650 is reconstructed using the tagged magnetic resonance data 642. Then in step 706 a control magnitude image 652 is reconstructed using the control magnetic resonance data 646. Then in step 708 the ASL image 654 is constructed by subtracting the control magnitude image 652 and the tagged magnitude image 650 from each other. In step 710 a series of magnetic resonance fingerprinting images 656 are reconstructed using the first portion of the fingerprinting magnetic resonance data 644 and/or the second portion of the fingerprinting magnetic resonance data 648. Finally in step 712 at least one magnetic resonance parametric map 658 is generated or calculated by comparing the series of magnetic resonance fingerprinting images 656 with the magnetic resonance fingerprinting dictionary 660.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 tagging pulse sequence commands
102 tagging inversion pulse portion
104 background suppression portion
104' background suppression portion
106 image acquisition portion
108 labeling duration
110 post labeling delay
200 background pulse sequence commands
202 control inversion portion
300 flip angle
302 pulse repetition
304 background suppression pulse sequence commands
306 MRF pulse sequence commands
500 delay
600 magnetic resonance system
604 magnet
606 bore of magnet
608 imaging zone
609 region of interest
610 magnetic field gradient coils
612 magnetic field gradient coil power supply
614 radio-frequency coil
616 transceiver
618 subject
620 subject support
630 computer system
632 hardware interface
634 processor
638 computer memory
640 machine executable instructions
642 tagged magnetic resonance data
644 first portion of fingerprinting magnetic resonance data
646 control magnetic resonance data
648 second portion of fingerprinting magnetic resonance data
650 tagged magnitude image
652 control magnitude image
654 ASL image
656 series of magnetic resonance fingerprinting images
658 magnetic resonance parametric map
660 magnetic resonance fingerprinting dictionary
700 acquire tagged magnetic resonance data and a first portion of the fingerprinting magnetic resonance data by controlling the magnetic resonance imaging system with the tagging pulse sequence commands
702 acquire control magnetic resonance data and a second portion of the fingerprinting magnetic resonance data by controlling the magnetic resonance imaging system with the control pulse sequence commands
704 reconstruct a tagged magnitude image using the tagged magnetic resonance data
706 reconstruct a control magnitude image using the control magnetic resonance data
708 construct an ASL image by subtracting the control magnitude image and the tagged magnitude image from each other
710 reconstruct a series of magnetic resonance fingerprinting images using the first portion of the fingerprinting magnetic resonance data and/or the second portion of the fingerprinting magnetic resonance data
712 generate at least one magnetic resonance parametric map by comparing the series of magnetic resonance fingerprinting images with a magnetic resonance fingerprinting dictionary

The invention claimed is:
1. A magnetic resonance imaging system for imaging a subject, wherein the magnetic resonance imaging system comprises:

a memory for storing machine executable instructions and pulse sequence commands, wherein the pulse sequence commands comprise:

tagging pulse sequence commands comprising a tagging inversion pulse portion for spin labeling a tagging location within the subject, a first background suppression portion, and a first image acquisition portion, wherein the first background suppression portion comprises first magnetic resonance fingerprinting (MRF) pulse sequence commands for acquiring a first portion of fingerprinting magnetic resonance data according to a magnetic resonance fingerprinting protocol; and control pulse sequence commands comprising a control inversion pulse portion, a second background suppression portion, and a second image acquisition portion, wherein the second background suppression portion comprises second MRF pulse sequence commands for acquiring a second portion of fingerprinting magnetic resonance data according to the magnetic resonance fingerprinting protocol;

and a processor for controlling the magnetic resonance imaging system, wherein execution of the machine executable instructions causes the processor to:

acquire tagged magnetic resonance data by controlling the magnetic resonance imaging system with the tagging pulse sequence commands according to a conventional arterial spin labeling protocol, and execute the first background suppression portion to acquire the first portion of fingerprinting magnetic resonance data;

acquire control magnetic resonance data by means of a conventional arterial spin labeling protocol by controlling the magnetic resonance imaging system with the control pulse sequence commands according to the conventional arterial spin labeling protocol, and execute the second background suppression portion to acquire the second portion of fingerprinting magnetic resonance data;

reconstruct tagged magnitude images using the tagged magnetic resonance data;

reconstruct control magnitude images using the control magnetic resonance data;

construct an arterial spin labeling (ASL) ASL image by subtracting the control magnitude images from the tagged magnitude images from each other;

reconstruct a series of magnetic resonance fingerprinting images using the first portion of fingerprinting magnetic resonance data and/or the second portion of fingerprinting magnetic resonance data; and generate at least one magnetic resonance parametric map by comparing the series of magnetic resonance fingerprinting images with a magnetic resonance fingerprinting dictionary.

2. The magnetic resonance imaging system of claim 1, wherein at least one of the first background suppression portion or second background suppression portion further comprises background suppression pulse sequence commands.

3. The magnetic resonance imaging system of claim 2, wherein the background suppression portion is discretely divided into regions of the background suppression pulse sequence commands and at least one region of the MRF pulse sequence commands.

4. The magnetic resonance imaging system of claim 3, wherein the tagging pulse sequence commands and control pulse sequence commands comprise a delay between a last portion of the at least one region of the MRF pulse sequence commands and the image acquisition portion.

5. The magnetic resonance imaging system of claim 1, wherein the MRF pulse sequence commands comprise a flip angle portion.

6. The magnetic resonance imaging system of claim 5, wherein the flip angle portion in the MRF pulse sequence commands of the tagging pulse sequence commands and the MRF pulse sequence commands of the control pulse sequence commands are identical.

7. The magnetic resonance imaging system of claim 5, wherein the flip angle portion is configured for generating flip angles below any one of the following: 10 degrees, 8 degrees, 7 degrees, 6 degrees, and 5 degrees.

8. The magnetic resonance imaging system of claim 1, wherein the at least one magnetic resonance parametric map comprises angiography data.

9. The magnetic resonance imaging system of claim 1, wherein the MRF pulse sequence commands of the tagging pulse sequence commands comprise a first gradient encoding portion, wherein the MRF pulse sequence commands of the control pulse sequence commands comprise a second gradient encoding portion, wherein the first gradient encoding portion and the second gradient encoding portion encode identical portions of k-space.

10. The magnetic resonance imaging system of claim 9, wherein execution of the machine executable instructions further cause the processor to calculate averaged magnetic resonance data by averaging corresponding elements of the first portion of the fingerprinting magnetic resonance data with the second portion of the fingerprinting magnetic resonance data, wherein the series of magnetic resonance fingerprinting images is reconstructed using the averaged magnetic resonance data.

11. The magnetic resonance imaging system of claim 1, wherein the MRF pulse sequence commands of the tagging pulse sequence commands comprise a first gradient encoding portion, wherein the wherein the MRF pulse sequence commands of the control pulse sequence commands comprise a second gradient encoding portion, wherein the first gradient encoding portion and the second gradient encoding portion encode interleaving portions of k-space.

12. The magnetic resonance imaging system of claim 1, wherein the ASL image comprises a cerebral blood flow map, wherein the magnetic resonance fingerprinting dictionary is a function of cerebral blood flow, wherein execution of the machine executable instructions causes the processor to use the cerebral blood flow map to provide the cerebral blood flow to the magnetic resonance fingerprinting dictionary during determination of the at least one magnetic resonance parametric map.

13. The magnetic resonance imaging system of claim 12, wherein the at least one magnetic resonance parametric map comprises any one of the following: a T2 map, a T1 map, an MTT map, and combinations thereof.

14. A computer program product comprising machine executable instructions stored on a non-transitory computer readable medium for execution by a processor controlling a magnetic resonance imaging system, wherein execution of the machine executable instructions causes the processor to:

acquire tagged magnetic resonance data by controlling the magnetic resonance imaging system with tagging pulse sequence commands according to a conventional arterial spin labeling protocol, wherein the tagging pulse sequence commands include a tagging inversion pulse portion for spin labeling a tagging location within the subject, a first background suppression portion, and a first image acquisition portion, wherein the first background suppression portion comprises first magnetic resonance fingerprinting (MRF) pulse sequence commands for acquiring a first portion of fingerprinting magnetic resonance data according to a magnetic resonance fingerprinting protocol;

acquire control magnetic resonance data by controlling the magnetic resonance imaging system with the control pulse sequence commands according to the conventional arterial spin labeling protocol, wherein the control pulse sequence commands include a control inversion pulse, a second background suppression portion, and a second image acquisition portion, wherein the second background suppression portion comprises second MRF pulse sequence commands for acquiring a second portion of fingerprinting magnetic resonance data according to the magnetic resonance fingerprinting protocol;

reconstruct tagged magnitude images using the tagged magnetic resonance data;

reconstruct control magnitude images using the control magnetic resonance data;

construct an ASL image by subtracting the control magnitude images and the tagged magnitude images from each other;

reconstruct a series of magnetic resonance fingerprinting images using the first portion of the fingerprinting magnetic resonance data and/or the second portion of the fingerprinting magnetic resonance data; and generate at least one magnetic resonance parametric map by comparing the series of magnetic resonance fingerprinting images with a magnetic resonance fingerprinting dictionary.

15. A method of operating a magnetic resonance imaging system for imaging a subject, wherein the method comprises:

acquiring tagged magnetic resonance data by controlling the magnetic resonance imaging system with tagging pulse sequence commands according to a conventional arterial spin labeling protocol, wherein the tagging pulse sequence commands include a tagging inversion pulse portion for spin labeling a tagging location within the subject, a first background suppression portion, and a first image acquisition portion, wherein the first background suppression portion comprises first magnetic resonance fingerprinting (MRF) pulse sequence commands for acquiring a first portion of fingerprinting magnetic resonance data according to a magnetic resonance fingerprinting protocol;

acquiring control magnetic resonance data by controlling the magnetic resonance imaging system with the control pulse sequence commands according to the conventional arterial spin labeling protocol, wherein the control pulse sequence commands include a control inversion pulse, a second background suppression portion, and a second image acquisition portion, wherein the second background suppression portion comprises second MRF pulse sequence commands for acquiring a second portion of fingerprinting magnetic resonance data according to the magnetic resonance fingerprinting protocol;

reconstructing tagged magnitude images using the tagged magnetic resonance data;

reconstructing control magnitude images using the control magnetic resonance data;

constructing an ASL image by subtracting the control magnitude images and the tagged magnitude images from each other;

reconstructing a series of magnetic resonance fingerprinting images using the first portion of the fingerprinting magnetic resonance data and/or the second portion of the fingerprinting magnetic resonance data; and generating at least one magnetic resonance parametric map by comparing the series of magnetic resonance fingerprinting images with a magnetic resonance fingerprinting dictionary.

* * * * *